United States Patent [19]

Petigara

[11] 4,310,590

[45] Jan. 12, 1982

[54] 3-ISOTHIAZOLONES AS BIOCIDES

[75] Inventor: Ramesh B. Petigara, Hatfield, Pa.

[73] Assignee: Rohm and Haas Company, Philadelphia, Pa.

[21] Appl. No.: 107,006

[22] Filed: Dec. 26, 1979

[51] Int. Cl.$^3$ .......................................... C07D 275/02
[52] U.S. Cl. .................................. 424/270; 548/213; 546/209; 424/245
[58] Field of Search ................ 424/270, 245; 548/213; 546/209

[56] References Cited
PUBLICATIONS

Ex parte Lewis 197 USPQ543.

Primary Examiner—Nicholas S. Rizzo

[57] ABSTRACT

Disclosed novel substituted 3-isothiazolones, salts thereof, metal complexes thereof, their preparation, agricultural compositions containing them, and their utilization in the control of living organisms. In particular, novel 5-(substituted thiocarbamoyl)thio-2-substituted-4-isothiazolin-3-ones and related compounds including 5-piperidino and 5-cyano derivatives are disclosed.

30 Claims, No Drawings

3-ISOTHIAZOLONES AS BIOCIDES

This invention relates to novel substituted 3-isothiazolones, salts thereof, metal complexes thereof, their preparation, agricultural compositions containing them, and their utilization in the control of living organisms.

These novel 3-isothiazolones (hereinafter referred to at times as "isothiazolones") are represented by the formula

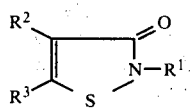

wherein
- $R^1$ is an unsubstituted or substituted alkyl, alkenyl, or alkynyl group of 1 to 18 carbon atoms, preferably 4 to 18 carbon atoms, an unsubstituted or substituted cycloalkyl group having a 3 to 12 carbon atom ring, an unsubstituted or substituted aralkyl group of up to 10 carbon atoms, or an unsubstituted or substituted aryl group of up to 10 carbon atoms, and is preferably alkyl or aralkyl;
- $R^2$ is hydrogen, halogen, or a $(C_1-C_4)$ alkyl group, preferably methyl ethyl, propyl, isopropyl, butyl, or t-butyl, especially methyl; and
- $R^3$ is —CN,

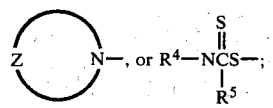

in which
- $R^4$ and $R^5$ are, independently, alkyl, aryl, or aralkyl, preferably $(C_1-C_8)$ alkyl, or aryl or aralkyl of up to 10 carbon atoms, or together form a saturated cycloimino group, preferably containing 4 to 6 carbon atoms; and
- Z is $(-CH_2-)_n$, n being from 4 to 6, preferably 4 or 5.

The alkyl substituents represented by $R^1$, $R^2$, and $R^3$ can have either branched- or straight-chain spatial configuration.

By a substituted alkyl group is means an alkyl group having one or more of its hydrogen atoms replaced by another substituent group. Examples of the substituted alkyl groups which characterize 3-isothiazolones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituted aralkyl groups which characterize 3-isothiazolones of this invention include halogen-, lower alkyl-, or lower alkoxy-substituted aralkyl groups, and the like.

By a substituted aryl group is meant an aryl group, such as benzene, naphthalene, or pyridine, having one or more of the hydrogen atoms on the aryl ring replaced by another substituent group. Examples of such substituent groups include halogen, nitro, lower alkyl, lower alkylacylamino, lower carbalkoxy, sulfamyl, and the like.

Representative $R^1$ substituents include methyl, ethyl, propyl, isopropyl, butyl, hexyl, octyl, decyl, pentadecyl, octadecyl, cyclopropyl, cyclohexyl, benzyl, 3,4-dichlorobenzyl, 4-methoxybenzyl, 4-chlorobenzyl, 3,4-dichlorophenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, allyl, propynyl, vinyl carboxyethyl, 1-isothiazolonylethyl, and 1,2,2-trichlorovinyl.

Representative $R^2$ substituents include hydrogen, bromo, chloro, iodo, methyl, ethyl, propyl, isopropyl, butyl and t-butyl.

Representative $R^3$ substituents are cyano, (N,N-dimethylthiocarbamoyl)thio-, (N,N-dibenzylthiocarbamoyl)thio-, piperidino-, and (N,N-tetramethylenethiocarbamoyl)thio-.

The isothiazolones described above can form acid salts, in the manner taught by U.S. Pat. No. 4,105,431, to Lewis et al., which salts also exhibit biocidal activity. Preparation of these biocidally active salts is readily achieved by reacting the above designated 3-isothiazolones with a strong inorganic or organic acid. Typical strong acids include hydrochloric, nitric, sulfuric, hydrobromic, chlorosulfuric, chloroacetic, oxalic, maleic, succinic, p-toluenesulfonic, and the like. Separation of the acid salts from the reaction medium is accomplished by any convenient means known to one skilled in the art.

Furthermore, metal salt complexes of the above isothiazolones are also useful as biocides. They have the formula:

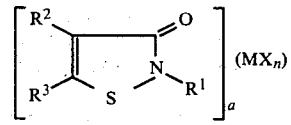

wherein
- $R^1$, $R^2$, and $R^3$ are as defined above,
- M is a cation of a metal, such as barium, cadmium, calcium, chromium, cobalt, copper, iron, lead, magnesium, manganese, mercury, nickel, strontium, tin, zinc, or the like;
- X is an anion forming a compound with the cation M, wherein the compound has sufficient solubility to form a metal salt complex;
- a is the integer 1 or 2; and
- n is an integer which for the anion X satisfies the valence of the cation M.

Among the anions which X can represent are chloride, bromide, iodide, sulfate, nitrate, nitrite, acetate, chlorate, perchlorate, bisulfate, bicarbonate, oxalate, maleate, p-toluenesulfonate, carbonate, phosphate, and the like. The preferred metals from which M is derived are calcium, copper, magnesium, manganese, nickel, and zinc. Among the metal cations embraced by M are cationic complexes of the metal ions, including complexes with ammonia, simple organic amines, and various heterocyclic organic amines such as pyridines, pyrimidines, and the like.

A wide variety of metal nitrates and the metal nitrites can be used to stabilize solutions of isothiazolones and generally any metal nitrate or nitrite which has appreciable solubility in the solution will exert a stabilizing effect. Among the useful metal nitrates are calcium nitrate, magnesium nitrate, copper nitrate, ferric nitrate, ferrous nitrate, nickel nitrate, zinc nitrate, barium nitrate, manganese nitrate, silver nitrate, cobalt nitrate, and the like. In a preferred embodiment of the invention, a metal nitrate is used to stabilize the isothiazolone solution. Surprisingly, other common metal salts, including carbonates, sulfates, chlorates, perchlorates, and chlorides are ineffective in stabilizing isothiazolones solutions.

Generally, the metal nitrate or nitrate is used to stabilize the isothiazolone solution in an amount of about 1 to about 30%, preferably about 15 to about 25%, by weight based on the weight of the solution. For example, in a 25% by weight solution of an isothiazolone, about 10 to about 30% by weight of the metal nitrate or nitrite will generally be sufficient to stabilize the solution against chemical decomposition. Of course, the amount of metal nitrate or nitrite needed to stabilize the solution will be partly dependent on the solvent, the isothiazolone and its concentration, the nitrate or nitrite used, the length of time the solution is to be kept, and other related factors.

The metal nitrates and metal nitrites are used to stabilize solutions of 3-isothiazolones in water and in polar organic solvents, including alcohols such as methanol, ethanol, propanol, butanol, ethylene glycol, propylene glycol, dipropylene glycol, polypropylene glycol, polyethylene glycol, 2-methoxyethanol, and the like. Among the applications in which solution of isothiazolones are used are as water-cooling system microbicides, as preservatives for aqueous dispersions of organic polymers, as wood pulp white water slimicides, as cosmetic preservatives, as cutting oil, jet fuel, and heating oil preservatives, and the like. Solutions of isothiazolones are also often used applying an isothiazolone to a solid substrate, such as fabric, leather, or wood, as a preservative, especially in automated treating processes.

When solutions of metal salt complexes of the isothiazolones are to be used, it may be advantageous to prepare the complexes in situ by neutralization of a salt, such as the hydrochloride salt, of the appropriate isothiazolone with a basic metal compound, such as an oxide or carbonate. Optionally, up to about one half mole equivalent of a metal nitrate is added to these solutions, prior to the addition of the metal nitrate stabilizer.

The metal salt complexes are made by the procedure of U.S. Pat. No. 4,067,878, to Miller et al., for instance.

Antibacterial and antifungal activity were evaluated by the Serial Dilution Test (Broth Titer Test) wherein a series of broths containing varying dilutions of a test compound and an organism are halved starting with 1:1,000. The values shown represent the maximum dilution in parts per million at which the compound under evaluation renders complete control of the organism. *Pseudomonas aeruginosa* (P), *Staphylococcus aureus* (S), and *Escherichia coli* (E) were the bacterial organisms employed in this test, and the fungi employed were *Aspergillus niger* (A) and *Rhizopus stolonifer* (R).

The compounds, acid addition salts, and metal salt complexes of this invention are broad-spectrum fungicides which possess activity against assorted phytopathogenic fungi, particularly in agricultural loci. These compounds, salts and complexes are particularly effective at rates of application of from about 50 to about 2000 ppm of the agronomically acceptable carrier in controlling phytopathogenic fungi such as barley net blotch (*Helmin-thosporium teres*) on barley plants (var. Wong), grey mold (*Botrytis fabae*) on faba beans (var. Vica faba), bean powdery mildew (*Erysiphe polygoni*) on bean plants (var. Dwarf Hort), grape downy mildew (*Plasmopora viticola*) on grape seedlings (var. Siebel 1000), rice blast (*Piricularia oryzae*) on rice plants (var. Nova 66), tomato late blight (*Phytophthora infestans*) on tomato seedlings (var. Rutgers), and wheat stem rust (*Puccinia graminis f.* sp. *tritici* race 15B-2) on wheat seedlings (var. Monon).

In evaluating these compounds, a preliminary fungicidal evaluation is carried out by applying the compounds at an application rate of 300 ppm based on liquid carrier and spraying the plants (previously inoculated with spores of the fungi and incubated under standard conditions) to run off in a carrier volume of about 150 gallons/acre. The test conditions are described in Chan et al. U.S. Pat. No. 4,157,576.

The general procedure is to take potted plants in proper condition of growth for susceptibility to the fungal disease to be evaluated, to spray these plants on a moving belt with the compound to be evaluated, and allow them to dry. The proper plants are then inoculated with the fungal spores and then allowed to incubate until the disease has developed and the percent control is read or estimated.

Generally, control of a living organism is achieved in accordance with this invention by contacting the organism with a compound of the invention in an amount which is effective to control the organism. Any of the techniques known in the art can be employed to disseminate the compound in a manner so as to achieve the desired contact with the organism to be controlled. Spraying and fumigating are typical of such techniques.

The compounds of this invention can be utilized as slimicides, algaecides, bactericides, fungicides or combinations thereof in any locus and particularly in aqueous media, such as, for example, water-cooling systems, swimming pools, protective or decorative films, crop seeds, soil, growing plants, paper pulp processes, aqueous polymer dispersions, water-based paints, and the like. In addition, these compounds and/or compositions containing them can function as fabric, paper, wood, and leather preservatives, cosmetic preservatives, soap additives, sanitizing agents, such as in laundry wash water, soaps and detergents, preservatives for metal working compounds, such as emulsifiable cutting oils, preservatives for fuels, fiber spin finish biocides, and the like.

In general, a locus subject to attack by microorganisms can be protected in accordance with this invention by incorporating into the locus a compound of the invention in an amount which is effective to control the microorganisms. The term "contamination" is meant to include any attack by microorganisms which leads to a chemical or physical breakdown or disintegration of the locus as well as the proliferation of the microorganisms within the locus without an accompanying deleterious effect. The exact amount required will, of course, vary with the medium being protected, the microorganisms being controlled, the particular compositions being employed, and the like. Typically, in a liquid medium, excellent control is obtained when the compounds are incorporated in the range of 0.1 to 10,000 parts per million (ppm.) or 0.00001 to 1% based on the weight of the medium. A range of 1 to 2000 ppm. is preferred.

The term "control", as employed in the specification and claims of this application, is to be construed as the effect of any means which adversely affects the existence or growth of any living organism or microorganism. This effect may comprise a complete killing action, eradication, arresting in growth, inhibition, reduction in number, or any combination of these effects.

The compounds of the invention are especially useful as agricultural fungicides. As such, they are particularly valuable when formulated in a fungicidal composition. Such compositions normally comprise an agronomically acceptable carrier and the compounds disclosed herein as the active agent or agents. Where necessary or desirable, surfactants or other additives may be incorporated to give uniformly formulated mixtures. By "agronomically acceptable carrier" is meant any substance which can be utilized to dissolve, dispense or diffuse the chemical incorporated therein without impairing the effectiveness of the toxic agent and which does no permanent damage to such environment as soil, equipment, and agronomic crops.

For use as pesticides, the compounds of this invention are usually taken up in an agronomically acceptable carrier or formulated so as to render them suitable for subsequent dissemination. For example, the amides may be formulated as wettable powders, emulsion concentrates, dusts, granular formulations, aerosols or flowable emulsifiable concentrates. In such formulations, the compounds are extended with a liquid or solid carrier and, when desired, suitable surfactants are likewise incorporated.

Compounds of this invention can be dissolved in a water-miscible liquid such as ethanol, isopropanol, acetone, and the like. Such solutions are easily extended with water.

The compounds of the invention can be taken up on or mixed with a fine particles of solid carriers, such as, for example, clays, inorganic silicates, carbonates, or silicas. Organic carriers can also be employed. Dust concentrates are commonly made wherein the compounds are present in the range of 20 to 80%. For ultimate applications these concentrates are normally extended with additional solid, to give an active ingredient content of from about 1 to 20%.

Wettable powder formulations are made by incorporating the compounds of this invention in an inert, finely divided solid carrier along with a surfactant which may be one or more emulsifying, wetting, dispersing or spreading agents or blend of these. The active compounds are usually present in the range of 10 to 80% by weight and the surfactants in from 0.5 to 10% by weight. Commonly used emulsifying and wetting agents include polyoxyethylated derivatives of alkylphenols, fatty alcohols, fatty acids and alkylamines; alkylarene sulfonates, and dialkyl sulfosuccinates. Spreading agents include such materials as glycerol mannitan laurate and condensates of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate a solid carrier by means of a solution of the compound in volatile solvent, such as acetone. In this manner, adjuvants, such as activators, adhesives, plant nutrients, synergists and various surfactants, may also be incorporated.

Emulsifiable concentrate formulations can be prepared by dissolving the compounds of the invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents generally constitute about 0.5 to 10% by weight of the emulsifiable concentrate and can be anionic, cationic or nonionic in character. Anionic surfactants include alcohol sulfates or sulfonates, alkylarene sulfonates and sulfosuccinates. Cationic surfactants include fatty acids alkyl amine salts and fatty acid alkyl quaternaries. Non-ionic emulsifying agents include ethylene oxide adducts of alkylphenols, fatty alcohols, mercaptans and fatty acids. The concentration of the active ingredients generally varies from about 10 to 80%, preferably in the range of about 25 to 50%.

For use as bactericides and fungicides, dilute sprays can be applied at concentrations of generally about 0.05 to 20 pounds of the active acrylamide ingredient per 100 gallons of spray. They are usually applied at 0.1 to 10 pounds per 100 gallons and preferably at 0.125 to 5 pounds per 100 gallons. In more concentrated sprays, the active ingredient is increased by a factor of 2 to 12. With dilute sprays, applications are usually made to the plants until run-off is achieved, whereas with more concentrated or low-volume sprays the materials are applied as mists.

The compounds of this invention can be utilized as the sole biocidal agents or they can be employed in conjunction with other fungicides, bactericides, algaecides, slimicides, mildewcides, insecticides, nematocides, and other comparable pesticides.

The products are prepared by means of a facile displacement of the chlorine in 5-chloro-2-methyl-4-isothiazolin-3-one with an (N,N-dimethylthiocarbamoyl)thio moiety when treated with N,N-dimethyldithiocarbamic acid, sodium salt, in an aqueous or ethanolic solution. This led to the synthesis of a series of novel 5-(N,N-dimethylthiocarbamoyl)thio-2-substituted-4-isothiazolin-3-ones starting from the 5-chloro derivatives. This action may be represented by:

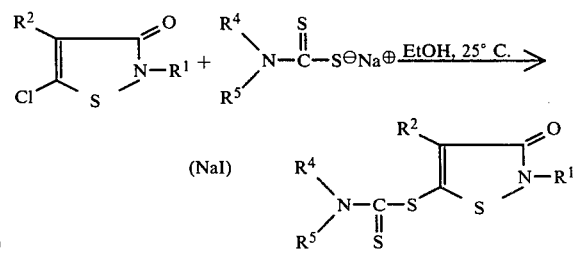

In the above, $R^1$, $R^2$, $R^4$, and $R^5$, have the meanings given above.

In place of sodium iodide, potassium iodide may be used. Other useful solvents include methanol, isopropanol, acetone, methylethyl ketone or a polar solvent, including water. The potassium salt of the dithiocarbamic acid is also useful. The temperature of the synthesis is from about 10° to about 40° C., preferably about room temperature.

A methyl group in the 4-position of the isothiazolone ring (with S in the 1-position, numbering being counter-clockwise) facilitated the chlorine displacement reaction, whereas a chlorine in that position retarded the reaction: $CH_3 > H > Cl$. In the absence of a 4-alkyl group a competing nucleophilic attack on S took place, leading to isothiazolone ring cleavage. A phenyl group or a cyclohexyl group in the 2-position favored this side reaction, whereas aralkyl and alkyl favored the chlorine displacement reaction.

Other dithiocarbamic acid salts obtained from the aliphatic or cyclic secondary amines also gave the desired 5-(substituted thiocarbamoyl)thio derivatives in moderate yields, e.g.:

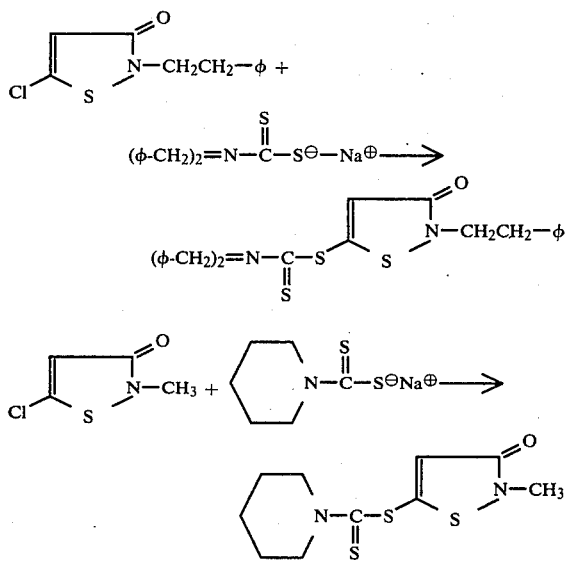

Reaction of the 5-chloro derivatives with a secondary amine gave, for example, a 5-piperidino derivative, and with sodium cyanide it gave the 5-cyano derivatives.

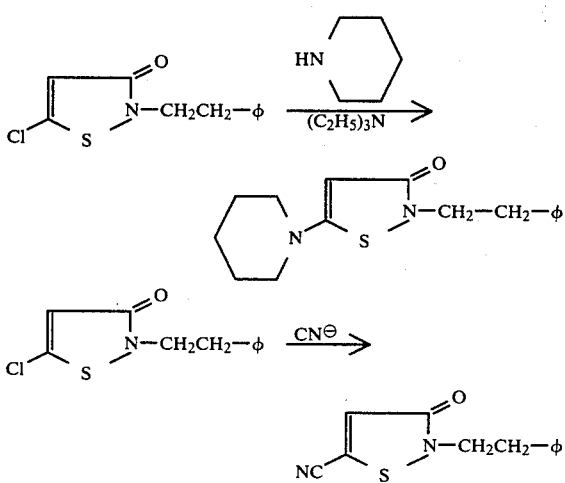

The starting 5-chloro isothiazolones were prepared as disclosed in U.S. Pat. Nos. 3,761,488 and 3,849,340 issued to Rohm and Haas Co., and as described in the publications [S. N. Lewis et al., *J. Heterocyclic Chemistry*, 8, 571(1971) and G. A. Miller et al., ibid, 8, 581(1971)].

The following are representative examples of procedures for obtaining the 5-substituted isothiazolone derivatives. In all instances the assigned structures were confirmed by elemental, IR and NMR analyses.

EXAMPLE 1

2-Benzyl-5-(N,N-dimethylthiocarbamoyl)thio-4-isothiazolin-3-one

To a solution of 6.76 g. (0.03 mole) of 2-benzyl-5-chloro-4-isothiazolin-3-one in 25 ml of ethanol was added a solution of 5.37 g. (0.03 mole) of N,N-dimethyldithiocarbamic acid sodium salt dihydrate in 30 ml of ethanol followed by 0.1 g. of sodium iodide. A yellow solid separated spontaneously. The mixture was stirred at room temperature for 3 hours, then cooled and filtered. The solid was triturated with 50 ml of water and recrystallized from 250 ml of boiling EtOH to give 5.6 g. (60% yield) of the named product, mp 184°–186°.

EXAMPLE 2

5-(N,N-Dimethylthiocarbamoyl)thio-4-methyl-2-phenyl-4-isothiazolin-3-one

To a solution of 4.51 g. (0.02 mole) of 5-chloro-4-methyl-2-phenyl-4-isothiazolin-3-one in 30 ml of warm ethanol was added a solution of 3.58 g. (0.02 mole) of N,N-dimethyldithiocarbamic acid, sodium salt dihydrate in 20 ml of ethanol followed by 0.1 g. of sodium iodide. The mixture was stirred several hours, cooled and filtered. The solid was triturated with water and dried to give 5.3 g. (88%) of the named product, mp 158°–160°.

EXAMPLE 3

4-Chloro-5-(N,N-dimethylthiocarbamoyl)thio-2-phenethyl-4-isothiazolin-3-one

To a solution of 5.48 g. (0.02 mole) of 4,5-dichloro-2-phenethyl-4-isothiazolin-3-one in 80 ml of ethanol was added 3.58 g. (0.02 mole) of N,N-dimethyldithiocarbic acid, sodium salt in 70 ml of ethanol followed by 0.15 g. sodium iodide. The mixture was stirred for 2 hours, cooled, and filtered. The solid was crystallized from 150 ml of boiling EtOH to give 1.7 g. (24%) of the named product, mp 125°–127°.

EXAMPLES 4–11

These products, shown in the tables, were prepared similarly to the products of Examples 1–3.

EXAMPLE 12

5-(N,N-Dibenzylthiocarbamoyl)thio-2-phenethyl-4-isothiazolin-3-one (a) N,N-Dibenzyldithiocarbamic acid sodium salt To a solution of 8.0 g. (0.2 mole) of sodium hydroxide in 32 ml of water was added 39.4 g. (0.2 mole) of dibenzyl amine. The mixture was cooled to 0° and to it was added 25.3 g. (0.334 mole) of carbon disulfide. A solid separated spontaneously. The mixture was stirred at room temperature for 1 hour, and then filtered. The solid was triturated first with 100 ml of ether and then with 100 ml of benzene and dried to give 43.5 g. (74% yield) of N,N-dibenzyldithiocarbamic acid sodium salt, mp 260°.

Anal. Calcd. for C$_{15}$H$_{14}$NS$_2$Na 2½ H$_2$O: C, 52.94; H, 5.58; N, 4.12; S, 18.80. Found: C, 52.91; H, 5.33; N, 4.58; S, 17.98.

(b) To a solution of 4.8 g. (0.02 mole) of 5-chloro-2-phenethyl-4-isothiazolin-3-one in 35 ml of ethanol was added 5.9 g. (0.02 mole) of N,N-dibenzyldithiocarbamic acid sodium salt followed by 0.15 g. sodium iodide. The mixture was concentrated in vacuo and the residue was treated with 300 ml of boiling hexane under reflux. The hexane solution decanted and cooled to give 0.63 g. of the named product, mp 98°–100°.

Anal. Calcd. for C$_{26}$H$_{24}$N$_2$OS$_3$: C, 65,51; H, 5.07; N, 5.88; S, 20.18. Found: C, 65.30; H, 5.19; N, 5.41; S, 19.73.

EXAMPLE 13

2-Methyl-5-[N,N-tetramethylenethiocarbamoyl]thio-4-isothiazolin-3-one (a) 1-Pyrrolidinecarbodithioc acid, sodium salt, dihydrate To a solution of 12.0 g. (0.3 mole) NaOH in 30 ml of water was added 21.34 g. (0.3 mole) of pyrroline. The mixture was cooled at 0° and to it 37.9 g. (0.5 mole) of CS$_2$ was added dropwise. A white solid separated spontaneously. The mixture was stirred for 15 minutes and then treated with 150 ml of ether. The solid was collected by filtration, triturated with 150 ml of ether, and dried at 50° in vacuum for 3 hours to give 55.2 g. of the product mp 260°.

Anal. Calcd. for C$_5$H$_8$NS$_2$Na 2H$_2$O: C, 29.27; H, 5.85; N, 6.83. Found: C, 29.20; H, 5.75; N, 7.52.

(b) To a solution of 3.0 g. (0.02 mole) of 5-chloro-2-methyl-4-isothiazolin-3-one in 30 ml of ethanol was added dropwise a solution of 4.1 g. (0.02 mole) of 1-pyrrolidine carbodithioic acid, sodium salt dihydrate in 60 ml of ethanol. A solid separated spontaneously, which was collected by filtration and recrystallized from 200 ml of ethanol to give 1.9 g. of a product. This was found to be a mixture of two products by TLC (silica gel, diisopropyl ether); Rf 0.0 (desired product) and Rf 0.43 (unknown). The mixture was separated on a dry column chromatograph (½"×20", silica gel) using diisopropyl ether. The product near the origin was eluted with 100 ml of CHCl$_3$. The solvent was removed to give 1.3 g. of the named product, mp 245°–250°.

Anal. Calcd. for C$_9$H$_{12}$N$_2$OS$_3$: C, 41.45; H, 4.61; N, 10.77; S, 36.92. Found: C, 41.89; H, 4.61; N, 10.82; S, 36.14.

Other compounds prepared in this series are given in the following table.

EXAMPLE 14

5-Piperidino-2-phenethyl-4-isothiazolin-3-one

A mixture of 2.4 g. (0.01 mole) of 5-chloro-2-phenethyl-4-isothiazolin-3-one, 0.85 g. (0.01 mole) of piperidine, 1.0 g. (0.01 mole) triethylamine and 0.1 g. sodium iodide in 10 ml of CHCl$_3$ was heated under reflux for 18 hours. The mixture was washed with water, dried (MgSO$_4$) and concentrated to dryness to give 2.7 g. of a liquid residue. This was purified by a dry column chromatography (1½×20", silica gel, diisopropyl ether) to give 1.0 g. of a solid product, which was recrystallized from 100 ml of diisopropyl ether to give 0.6 g of the named product, mp 106°–108°.

Anal. Calcd. for C$_{16}$H$_{20}$N$_2$OS: C, 66.63; H, 6.99; N, 9.71; S, 11.12. Found: C, 66.54; H, 7.20; N, 9.67; S, 11.02.

EXAMPLE 15

5-Cyano-2-phenethyl-4-isothiazolin-3-one

A mixture of 4.8 g. (0.02 mole) of 5-chloro-2-phenethyl-4-isothiazolin-3-one in 25 ml of CHCl$_3$, 1.0 g. (0.02 mole) of sodium cyanide in 5 ml of water and 0.015 g of tetrabutyl ammonium bromide was heated under reflux for 1 hour, while stirring. The mixture was then washed with water, dried, and concentrated to give a gummy brown residue, which was recrystallized from 300 ml of ethanol to give 0.15 g. of the named product, mp 228°–230 (softened at 210°).

Anal. Calcd. for C$_{12}$H$_{10}$N$_2$OS: C, 62.59; H, 4.38; N, 12.16; S, 13.92. Found: C, 62.61; H, 4.43; N, 11.93; S, 13.75.

Tables I and II give typical compounds and their analyses. Tables III and IV give examples of the use of the compounds as bactericides and fungicides or mildewcides, used in the manner described.

TABLE I $$\underset{(CH_3)_2N-\underset{\underset{S}{\|}}{C}S}{R^2}\diagdown\!\!\!\!\!\!\!\!\diagup\!\!\!\!\!\!\!\!\underset{S}{\diagdown}\!\!\!\!\!\!\!\!\diagup\!\!\!\!\!\!\!\!N\!\!-\!\!R^1\!\!=\!\!O$$

| Example | R$^2$ | R$^1$ | M.P. °C. | Recryst. Solvent | % Yield |
|---|---|---|---|---|---|
| 1 | H | —CH$_2$—⟨phenyl⟩ | 184–186 | EtOH | 60 |
| 2 | CH$_3$ | —⟨phenyl⟩ | 158–160 | — | 88 |
| 3 | Cl | —CH$_2$CH$_2$—⟨phenyl⟩ | 125–127 | EtOH | 24 |
| 4 | H | —CH$_2$CH$_2$—⟨phenyl⟩ | 146.5–147.5 | — | 50 |
| 5 | H | —CH$_3$ | 191–193 | EtOH | 34 |
| 6 | H | —C$_8$H$_{17}$—n | 98–100 | Me$_2$CO | 30 |
| 7 | CH$_3$ | —CH$_2$CH$_2$—⟨phenyl⟩ | 128–130 | EtOH | 60 |
| 8 | CH$_3$ | ⟨phenyl⟩—Br | 183–185 | — | 80 |
| 9 | CH$_3$ | ⟨phenyl⟩—Cl | 176–178 | — | 75 |
| 10 | CH$_3$ | ⟨phenyl with Cl, Cl⟩ | 178–180 | Me$_2$CO | 25 |
| 11 | CH$_3$ | ⟨phenyl-H⟩ | 111–113 | Me$_2$CO | 48 |

TABLE II

| | | Elemental Analysis Calculated/Found | | | | |
|---|---|---|---|---|---|---|
| Ex. | Empirical Formula | C | H | N | S | Halogen |
| 1 | C$_{13}$H$_{14}$N$_2$OS$_3$ | 50.29 | 4.55 | 9.02 | 30.99 | — |
| | | 50.22 | 4.65 | 9.10 | 30.15 | |
| 2 | C$_{13}$H$_{14}$N$_2$OS$_3$ | 50.29 | 4.54 | 9.02 | 30.98 | — |
| | | 49.89 | 4.50 | 9.13 | 30.26 | |
| 3 | C$_{14}$H$_{15}$ClN$_2$OS$_3$ | 46.85 | 4.21 | 7.80 | 26.80 | 9.88 |
| | | 46.26 | 4.26 | 7.60 | 26.17 | 9.70 |
| 4 | C$_{14}$H$_{16}$N$_2$OS$_3$ | 51.85 | 4.94 | 8.64 | 29.63 | — |
| | | 51.64 | 5.05 | 8.47 | 29.22 | |
| 5 | C$_7$H$_{10}$N$_2$OS$_3$ | 35.99 | 4.27 | 11.96 | 41.03 | — |

TABLE II-continued

| Ex. | Empirical Formula | Elemental Analysis Calculated/Found | | | | |
|---|---|---|---|---|---|---|
| | | C | H | N | S | Halogen |
| | | 35.85 | 4.27 | 11.94 | 40.33 | |
| 6 | $C_{14}H_{24}N_2OS_3$ | 50.57 | 7.27 | 8.42 | 28.93 | — |
| | | 50.36 | 7.46 | 8.76 | 28.31 | |
| 7 | $C_{15}H_{18}N_2OS_3$ | 53.22 | 5.36 | 8.28 | 28.42 | — |
| | | 53.33 | 5.40 | 8.28 | 27.90 | |
| 8 | $C_{13}H_{13}BrN_2OS_3$ | 40.10 | 3.27 | 7.19 | 24.71 | 20.52 |
| | | 39.98 | 3.32 | 7.31 | 23.52 | 21.30 |
| 9 | $C_{13}H_{13}ClN_2OS_3$ | 45.27 | 3.80 | 8.12 | 27.89 | 10.28 |
| | | 45.22 | 3.77 | 8.14 | 27.54 | 10.57 |
| 10 | $C_{13}H_{12}Cl_2N_2OS_3$ | 41.16 | 3.19 | 7.38 | 25.36 | 18.69 |
| | | 40.92 | 3.14 | 7.37 | 25.38 | 18.51 |
| 11 | $(C_{13}H_{20}N_2OS_3)_2 \cdot H_2O$ | 47.97 | 6.50 | 8.61 | 29.55 | — |
| | | 48.52 | 6.55 | 8.67 | 29.47 | — |

TABLE IV

| Ex-ample | Doses (ppm) | Disease[b] Control Level[c] | | | | | | |
|---|---|---|---|---|---|---|---|---|
| | | BH | BOT | BPM | GDM | RB | TLB | WSR |
| 1 | 300 | A | B | E | B | — | E | B |
| | 150 | E | B/B | | C/C | A/E | | C/C |
| | 75 | E | C | | C | A | | E |
| | 38 | E | C | | D | A | | E |
| 2 | 300 | E | B | E | E | — | E | C |

TABLE III
Biological Activity of 5-Substituted Isothiazolones

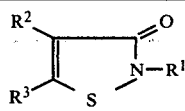

| Prod. of Ex. | $R^3$ | $R^2$ | $R^1$ | SDT,MIC in PPM[a] | | | | |
|---|---|---|---|---|---|---|---|---|
| | | | | E | P | S | A | R |
| 1 | $(CH_3)_2N-\overset{S}{\underset{\parallel}{C}}-S-$ | H | $-CH_2-\langle\bigcirc\rangle$ | — | — | >500 | — | — |
| 2 | $(CH_3)_2N-\overset{S}{\underset{\parallel}{C}}-S-$ | $CH_3$ | $-\langle\bigcirc\rangle$ | 500 | >500 | — | 500 | — |
| 3 | $(CH_3)_2N-\overset{S}{\underset{\parallel}{C}}-S-$ | Cl | $-CH_2CH_2-\langle\bigcirc\rangle$ | — | — | >500 | — | — |
| 4 | $(CH_3)_2N-\overset{S}{\underset{\parallel}{C}}-S-$ | H | $-CH_2CH_2-\langle\bigcirc\rangle$ | — | — | >500 | — | — |
| 5 | $(CH_3)_2N-\overset{S}{\underset{\parallel}{C}}-S-$ | H | $-CH_3$ | 500 | >500 | — | 125 | — |
| 6 | $(CH_3)_2N-\overset{S}{\underset{\parallel}{C}}-S-$ | H | $-C_8H_{17}-n$ | Not | tested | (NT) | | |
| 7 | $(CH_3)_2N-\overset{S}{\underset{\parallel}{C}}-S-$ | $CH_3$ | $-CH_2CH_2-\langle\bigcirc\rangle$ | — | — | >500 | — | — |
| 8 | $(CH_3)_2N-\overset{S}{\underset{\parallel}{C}}-S-$ | $CH_3$ | $\langle\bigcirc\rangle-Br$ | 500 | 500 | 500 | 500 | 250 |
| 9 | $(CH_3)_2-N-\overset{S}{\underset{\parallel}{C}}-S-$ | $CH_3$ | $\langle\bigcirc\rangle-Cl$ | 500 | 500 | 500 | 500 | 250 |
| 10 | $(CH_3)_2-N-\overset{S}{\underset{\parallel}{C}}-S-$ | $CH_3$ | $\langle\bigcirc\rangle\overset{Cl}{\underset{Cl}{}}$ | 500 | 500 | 500 | 500 | 250 |
| 11 | $(CH_3)_2-N-\overset{S}{\underset{\parallel}{C}}-S-$ | $CH_3$ | $\langle\bigcirc\rangle-H$ | 500 | 500 | 500 | 500 | 250 |
| 12 | $(C_6H_5CH_2)_2N-\overset{S}{\underset{\parallel}{C}}-S-$ | H | $-CH_2CH_2-\langle\bigcirc\rangle$ | | NT | | | |
| 13 | $\langle N\rangle-\overset{S}{\underset{\parallel}{C}}-S-$ | H | $-CH_3$ | — | — | >500 | — | — |
| 14 | $\langle N\rangle-$ | H | $-CH_2CH_2-\langle\bigcirc\rangle$ | 500 | 500 | 500 | 250 | 125 |
| 15 | $NC-$ | H | $-CH_2CH_2-\langle\bigcirc\rangle$ | — | — | >500 | — | — |

[a]In vitro serial dilution test (SDT), minimum inhibitory concentrations (MIC) against E = *E. coli*, P = *Ps. aeruginosa*, S = *Staphylococcus aureus*, A = *A. niger*, and R = *Rhizopus stolonifer* are given in parts per million of a biocide.

TABLE IV-continued

| Ex-ample | Doses (ppm) | BH | BOT | BPM | GDM | RB | TLB | WSR |
|---|---|---|---|---|---|---|---|---|
| | 150 | | B/C | | | A/E | | |
| | 75 | | B | | | B | | |
| | 38 | | C | | | B | | |
| 3 | 300 | E | E | E | E | E | E | C |
| 4 | 300 | E | B | E | B | — | E | A |
| | 150 | | A/C | | A/A | A | | E/E |
| | 75 | | B | | A | E | | — |
| | 38 | | B | | B | E | | — |
| 5 | 300 | A | B | E | B | — | E | B |
| | 150 | E | A/C | | A/A | A/E | | C/E |
| | 75 | E | A | | A | A | | E |
| | 38 | E | B | | A | A | | |
| | 19 | E | — | | C/E | A | | |
| 6 | 300 | E | E | E | E | — | — | A |
| 7 | 300 | E | E | E | E | — | E | A |
| | 150 | | | | | B/E | | E |
| | 75 | | | | | B | | E |
| | 38 | | | | | B | | E |
| 8 | 300 | E | C | E | B | — | E | B |
| | 150 | | | | A/B | A/E | | C/C |
| | 75 | | | | A | A | | C |
| | 38 | | | | B | A | | C |
| 9 | 300 | E | B | E | A | A | E | B |
| | 150 | | C/C | | A/E | A/A | | E |
| | 75 | | C | | E | A | | E |
| | 38 | | C | | E | A | | E |
| 10 | 300 | E | E | E | E | E | E | E |
| 11 | 300 | E | E | E | E | E | E | C |
| 12 | 300 | E | E | E | E | E | E | E |
| 13 | 300 | E | A | E | A | B | B | B |
| | 150 | | A/E | | A/E | A/E | A/E | C/E |
| | 75 | | C | | A | B | B | C |
| | 38 | | C | | A | B | E | C |
| 14 | 300 | E | E | E | E | A | E | A |
| | 150 | | | | | A/E | | E |
| | 75 | | | | | A | | E |
| | 38 | | | | | E | | E |
| 15 | | NT | | | | | | |

[b]BH-Barley net blotch (*Helminthosporium teres*), BOT-Chocolate spot of broad beans (*Botrytis cinerea*), BPM = Bean powdery mildew (*Erysiphe polygoni*), GDM = Grape downy mildew (*Plasmopora viticola*), RB = Rice blast (*Piricularia oryzae*), WSR = Wheat stem rust (*Puccinia graminis* f. sp. f. tritici).
[c]Ratings: A = 97-100% Disease Control, B = 90-96%; C = 70-89%; D = 50-69%; E = 50%.

I claim:
1. A compound of the formula

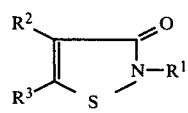

wherein
$R^1$ is an unsubstituted or substituted alkyl, alkenyl, or alkynyl group of 1 to 18 carbon atoms, an unsubstituted or substituted cycloalkyl group having a 3 to 12 carbon atom ring, an unsubstituted or substituted aralkyl group of up to 10 carbon atoms, or an unsubstituted or substituted aryl group of up to 10 carbon atoms, and is preferably alkyl or aralkyl;
$R^2$ is hydrogen, halogen, or ($C_1$-$C_4$) alkyl; and
$R^3$ is —CN,

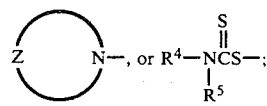

in which $R^4$ and $R^5$ are, independently, alkyl, aryl, or aralkyl, or aryl or aralkyl of up to 10 carbon atoms, or together from a saturated cycloimino group; and containing 4 to 6 carbon atoms Z is (—$CH_2$—)$_n$, n being an integer of from 4 to 6, preferably 4 or 5.

2. A salt of a compound of claim 1 of a strong acid selected from the group consisting of hydrochloric, nitric, sulfuric, hydrobromic, chlorosulfuric, chloroacetic, oxalic, maleic, succinic, and p-toluenesulfonic.

3. The compound of claim 1 in which $R^1$ is alkyl, cycloalkyl aryl, or aralkyl, $R^2$ is alkyl or chloro, and $R^3$ is selected from CN—,

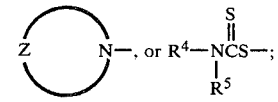

in which $R^4$ and $R^5$ are $C_1$-$C_8$ alkyl, or, together form a cycloimino group having 4 or 5 carbon atoms, and Z is (—$CH_2$)$_n$, n being 4 or 5.

4. A composition for controlling the growth of bacteria or fungi comprising an agronomically acceptable carrier and, in an amount which is effective to control said growth, the composition of claim 1, 2, or 3.

5. A method for controlling the growth of bacteria or fungi in a locus subject to contamination thereby, which comprises incorporating onto or into the locus, in an amount which is effective to control such growth, a compound, salt, or complex of claim 1, 2, or 3.

6. The method of claim 5 wherein the locus is an aqueous medium.

7. The method of claim 5 wherein the locus is a cutting oil formulation comprising a cutting oil, water, and an emulsifying agent.

8. The method of claim 5 wherein the locus is a water-cooling system.

9. The method of claim 5 wherein the locus is a solid protective or decorative film.

10. The method of claim 5 wherein the locus is fibrous in the form of fabric, leather, paper, or wood.

11. The method of claim 5 wherein the locus is laundry wash water.

12. The method of claim 5 in which the locus is a crop seed.

13. The method of claim 5 in which the locus is an agricultural growth medium.

14. The method of claim 5 in which the locus is a growing plant.

15. The method of claim 5 in which the locus is an agricultural environment.

16. A compound of claim 1 in which $R^1$, $R^2$, and $R^3$ have the following values

| $R^3$ | $R^2$ | $R^1$ |
|---|---|---|
| $(CH_3)_2N-\overset{S}{\overset{\|}{C}}-S-$ | H | —$CH_2$—⌬ |
| $(CH_3)_2N-\overset{S}{\overset{\|}{C}}-S-$ | $CH_3$ | —⌬ |
| $(CH_3)_2N-\overset{S}{\overset{\|}{C}}-S-$ | Cl | —$CH_2CH_2$—⌬ |
| $(CH_3)_2N-\overset{S}{\overset{\|}{C}}-S-$ | H | —$CH_2CH_2$—⌬ |

-continued

| R³ | R² | R¹ |
|---|---|---|
| (CH₃)₂N—C(=S)—S— | H | —CH₃ |
| (CH₃)₂N—C(=S)—S— | H | —C₈H₁₇—n |
| (CH₃)₂N—C(=S)—S— | CH₃ | —CH₂CH₂—C₆H₁₁ |
| (CH₃)₂N—C(=S)—S— | CH₃ | —C₆H₄—Br |
| (CH₃)₂—N—C(=S)—S— | CH₃ | —C₆H₄—Cl |
| (CH₃)₂—N—C(=S)—S— | CH₃ | —C₆H₃(Cl)(Cl) |
| (CH₃)₂—N—C(=S)—S— | CH₃ | —C₆H₅ |
| (C₆H₅CH₂)₂N—C(=S)—S— | H | —CH₂CH₂—C₆H₅ |
| (pyrrolidinyl)N—C(=S)—S— | H | —CH₃ |
| (piperidinyl)N— | H | —CH₂CH₂—C₆H₅ |
| NC— | H | —CH₂CH₂—C₆H₅ |

17. The compound of claim 16 in which R³ is $$(CH_3)_2N-\overset{S}{\underset{\|}{C}}-S-$$

R² is H and R¹ is —CH₃.

18. A salt of a compound of claim 16 or 17 of a strong acid selected from the group consisting of hydrochloric, nitric, sulfuric, hydrobromic, chlorosulfuric, chloroacetic, oxalic, maleic, succinic, and p-toluenesulfonic.

19. A composition for controlling the growth of bacteria or fungi comprising an agronomically acceptable carrier and, in an amount which is effective to control said growth, the composition of claim 16, 17, or 18.

20. A method for controlling the growth of bacteria or fungi in a locus subject to contamination thereby, which comprises incorporating onto or into the locus, in an amount which is effective to control such growth, a compound, salt, or complex of claim 16, 17, or 18.

21. The method of claim 20 wherein the locus is an aqueous medium.

22. The method of claim 20 wherein the locus is a cutting oil formulation comprising a cutting oil, water, and an emulsifying agent.

23. The method of claim 20 wherein the locus is a water-cooling system.

24. The method of claim 20 wherein the locus is a solid protective or decorative film.

25. The method of claim 20 wherein the locus is fibrous in the form of fabric, leather, paper, or wood.

26. The method of claim 20 wherein the locus is laundry wash water.

27. The method of claim 20 in which the locus is a crop seed.

28. The method of claim 20 in which the locus is an agricultural growth medium.

29. The method of claim 20 in which the locus is a growing plant.

30. The method of claim 20 in which the locus is an agricultural environment.

* * * * *

UNITED STATES PATENT AND TRADEMARK OFFICE
CERTIFICATE OF CORRECTION

PATENT NO. : 4,310,590
DATED : January 12, 1982
INVENTOR(S) : Ramesh B. Petigara It is certified that error appears in the above-identified patent and that said Letters Patent is hereby corrected as shown below:

Col. 14, line 3 - The word "from" should read -- form --.

Claim 16 - change all of these groups  under $R^1$ to  .

Signed and Sealed this

Twenty-eighth Day of February 1984

[SEAL]

Attest:

GERALD J. MOSSINGHOFF

Attesting Officer

Commissioner of Patents and Trademarks